US012217227B2

(12) United States Patent
Hummer (10) Patent No.: US 12,217,227 B2
(45) Date of Patent: *Feb. 4, 2025

(54) DATA PROCESSING FOR COST AND PRICE DETERMINATIONS WITH ELECTRONIC NEGOTIATION

(71) Applicant: Gregory J. Hummer, Shaker Heights, OH (US)

(72) Inventor: Gregory J. Hummer, Shaker Heights, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 18/655,304

(22) Filed: May 5, 2024

(65) Prior Publication Data

US 2024/0394674 A1    Nov. 28, 2024

Related U.S. Application Data

(63) Continuation of application No. 17/885,471, filed on Aug. 10, 2022, now Pat. No. 11,978,027.

(51) Int. Cl.
G06Q 20/10     (2012.01)
G06Q 20/08     (2012.01)
G16H 10/60     (2018.01)

(52) U.S. Cl.
CPC ......... *G06Q 20/102* (2013.01); *G06Q 20/085* (2013.01); *G16H 10/60* (2018.01)

(58) Field of Classification Search
CPC ..... G06Q 20/102; G06Q 20/085; G16H 10/60
See application file for complete search history.

*Primary Examiner* — Aryan E Weisenfeld
(74) *Attorney, Agent, or Firm* — Edmond DeFrank (57) ABSTRACT

The embodiments disclose a data processing cost and price determination platform with electronic negotiation, including a mobile app configured to register a medical patient, a medical database configured to retrieve patient demographics, patient medical necessity codes and patient billed account data related to the medical patient of a medical provider, a server configured to electronically collect updated patient medical pricing data from governmental and health insurance carrier sources and medical necessity standards based on demographics of the medical provider, a processor configured to compare the patient billed account with the updated medical pricing data to determine a suggested fair market of the patient billed account, an electronic negotiation module to submit the suggested fair market of the patient billed account data to the medical provider for soliciting a negotiated settlement rate and a communication module to transmit the accepted negotiated settlement rate from the medical provider to the medical patient.

20 Claims, 9 Drawing Sheets

EMPLOYER PUBLIC ACCESS - WORK WITH BILLS

EMPLOYEE: GREG H HUMMER

| | |
|---|---|
| BILL DATE: | 05/06/2013 |
| DATE OF SERVICE: | 05/06/2013 |
| PROVIDER INVOICE #: | 1234567 |
| PROVIDER: | JOE SMITH [v] UPDATE PROVIDER |
| | PROVIDER LETER 2 [v] |
| INSURANCE COMPANY: | AETNA [v] UPDATE INSURANCE COMPANY |
| BILL AMOUNT: | 500.00 |
| AMOUNT INSURANCE WILL PAY: | .00 |
| BALANCE DUE: | 500.00 |
| DUE DATE: | 00/00/0000 |
| AUTO CALCULATE AMOUNTS: | [ ] |
| TO PAY PROVIDER AMOUNT: | 400.00 |
| MEMBER BILL AMOUNT: | 33.33 |
| SERVICE FEE AMOUNT | |
| STATUS: | REVIEWED – SEND TO PROVIDER [v] |

410 — AUTO CALCULATE AMOUNTS
406 — TO PAY PROVIDER AMOUNT
408 — MEMBER BILL AMOUNT

CHANGE

DATA PROCESSING FOR COST AND PRICE DETERMINATIONS WITH ELECTRONIC NEGOTIATION

CROSS-REFERENCED TO RELATED APPLICATIONS

This patent application is a continuation of and claims priority to pending U.S. Non-Provisional application Ser. No. 17/885,471 filed Aug. 10, 2022, entitled "DATA PROCESSING FOR COST AND PRICE DETERMINATIONS WITH ELECTRONIC NEGOTIATION", by Gregory J. Hummer, which is a continuation-in-part application based on pending U.S. Non-Provisional application Ser. No. 14/296,650 filed Jun. 5, 2014, entitled "WEB-BASED AUTOMATED BILL NEGOTIATION SYSTEM", by Gregory J. Hummer, the U.S. patent application being incorporated herein by reference.

BACKGROUND

Data processing is used to collect the data and translate and analyze the data into usable information. Electronic negotiation is a method of allowing negotiations via electronic communications. Many forms of data processing involve a manual process to setup the data.

DETAILED DESCRIPTION OF THE INVENTION

In a following description, reference is made to the accompanying drawings, which form a part hereof, and in which is shown by way of illustration a specific example in which the invention may be practiced. It is to be understood that other embodiments may be utilized, and structural changes may be made without departing from the scope of the present invention.

General Overview:

It should be noted that the descriptions that follow, for example, in terms of a data processing for cost and price determinations with electronic negotiation are described for illustrative purposes and the underlying system can apply to any number and multiple types of billings. In one embodiment of the present invention, the data processing for cost and price determinations with electronic negotiation can be configured using an electronic negotiation mobile app. The data processing for cost and price determinations with electronic negotiation can be configured to include at least one remote server database and can be configured to include at least one remote server processor using the present invention.

According to one aspect, a data processing for cost and price determinations with electronic negotiation facilitates negotiating a patient's bill owed to a medical provider comprises a processor that executes computer-executable instructions for calculating a settlement amount on the patient's balance bill owed to the medical provider or may offer a prospective amount to the medical provider on behalf of the patient, therewith and a memory device 16 that stores the computer-executable instructions.

The data processing for cost and price determinations with electronic negotiation platform further includes a data processing for cost and price determinations with electronic negotiation server comprising a processor and a memory device and providing Internet access to the processor for calculating the settlement amount. The instructions comprise receiving patient billing information, calculating a settlement amount associated with the bill owed or an amount prospectively for the procedure to be owed to the medical provider from the patient billing information, electronically communicating the settlement amount to the associated medical provider, determining whether the medical provider accepted or declined the settlement amount, informing the patient and charging a service fee if the medical provider accepted the settlement amount, calculating a second settlement amount if the medical provider declined the settlement amount, electronically communicating the second settlement amount to the associated medical provider, determining whether the medical provider accepted or declined the second settlement amount, informing the patient and charging a service fee if the medical provider accepted the second settlement amount, and updating a bill status based on the determination of the first and second settlement amounts.

In accordance with various features described herein, systems and methods are described that facilitate the negotiation of a medical bill for an individual (e.g., patients and their family members, insurance customers, and their family members, etc.) via a web-based cloud application that automatically calculates the best settlement offer for the individual's bills. As used herein, "algorithm" or "module" refers to a set of computer-executable instructions stored on a computer-readable medium and executable by a processor or other computing device, as will be appreciated by those of skill in the art.

The terms data processing cost and price determination with electronic negotiation, data processing cost, and price determination with electronic negotiation are used interchangeably without any change in meaning.

Figure 1:
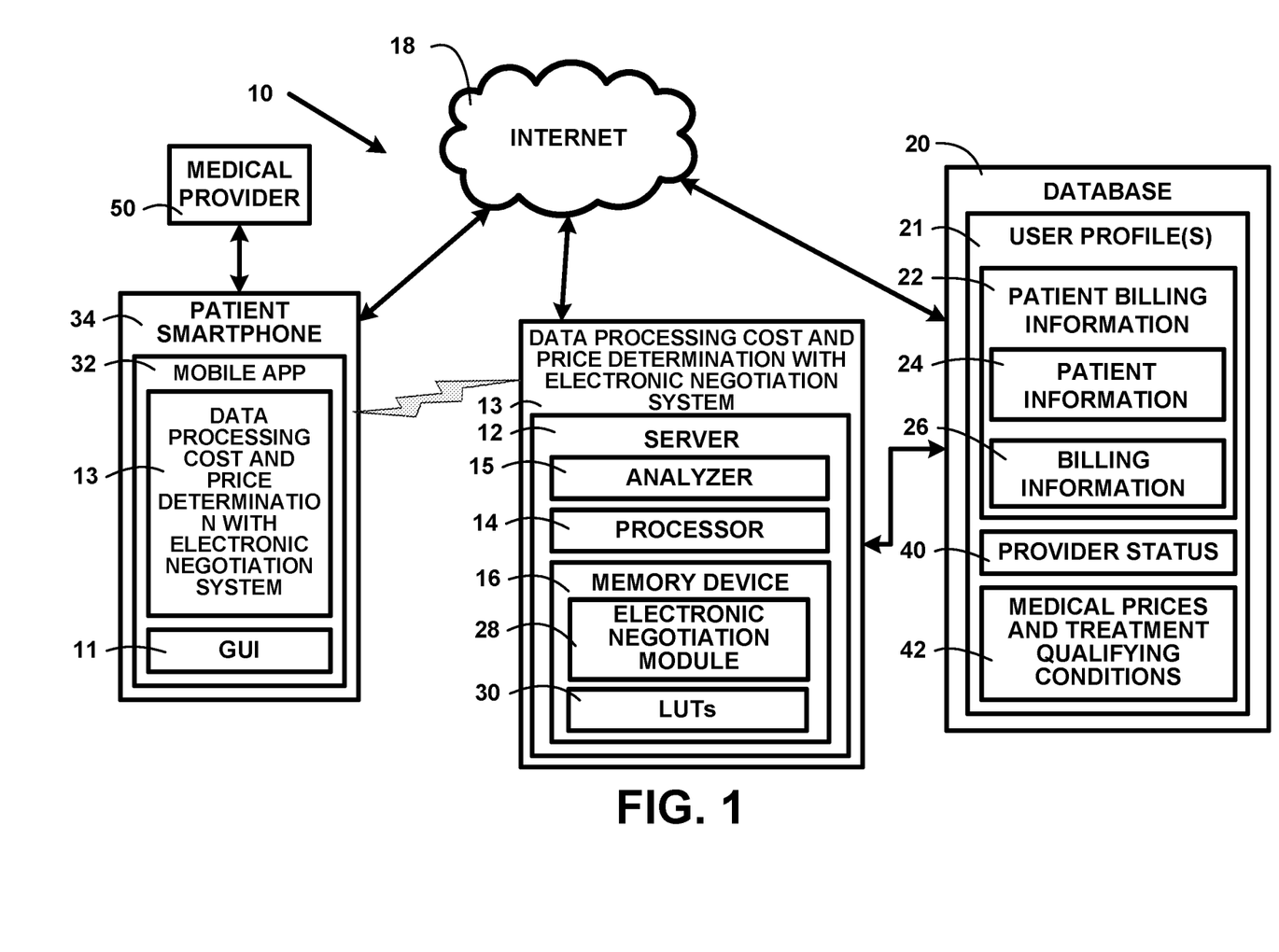
FIG. 1 illustrates a system for data processing cost and price determination with electronic negotiation, in accordance with various aspects set forth herein of one embodiment.

Graphical User Interface:

With reference to FIG. 1, a system 10 is illustrated that facilitates providing the herein-described data processing cost and price determination with electronic negotiation, e.g., via a graphical user interface (GUI) 11. The system 10 includes a data processing cost and price determination with electronic negotiation 13 server 12 with an analyzer 15 and a processor 14 that executes, and a memory device 16 that stores, computer-executable instructions for performing the various functions, methods, techniques, algorithms, etc., described herein. The server 12 is coupled to the Internet 18, by which it communicates with an electronic negotiation mobile app 32, accesses, etc., the GUI 11 of, for example, at least one device from a group consisting of a patient's personal computer, laptop, tablet, patient smartphone 34, Additionally, the server 12 can access a database 20 that stores user profiles 21 comprising patient billing information 22. The patient billing information 22 includes patient information 24 (e.g., patient name, patient contact information, medical provider 50, medical provider contact information, insurance carrier, insurance carrier account information, patient payment information, etc.) and billing information 26 (e.g., invoice number, bill amount, patient balance, date of service, negotiated amount to pay, status of the bill, due date, etc.). The database 20 also stores updates of the provider status 40 and medical prices and treatment qualifying conditions 42.

The patient billing information 22 may be entered by the user (e.g., via the GUI) or may be medical record data that the user has authorized to be made available to a provider of the automated bill negotiation. Although depicted as being stored in a database 20 coupled to the GUI and server 12 via the internet 18, the user profile can reside on the user's GUI 11 or at any other suitable location (e.g., the server 12, a remote server 12, or computer-readable storage device, etc.). In another embodiment, the database 20 is a distributed database, and/or the server 12 is a distributed server 12.

The patient billing information 22 is uploaded to, or retrieved by, the server 12 and loaded into a data processing cost and price determination with electronic negotiation 13 and electronic negotiation module 28 stored in the memory device 16. The electronic negotiation module 28 utilizes the patient billing information 22 to automatically secure a settlement or discount on the patient's balance bill owed to a medical provider 50. Specifically, the data processing cost and price determination with electronic negotiation 13 uses the electronic negotiation module 28 to calculate a settlement amount associated for each bill included in the patient billing information 22 to provide the greatest chance of success to decrease the amount owed to the medical provider 50.

The settlement amount is then communicated to the medical provider 50 whom either accepts or declines the settlement amount, by clicking on Accept or Decline within the email, which then automatically updates the server database 20 immediately or by e-faxing the offer back to the server 12. If the medical provider 50 accepts the settlement amount, the patient is then charged by the data processing cost and price determination with electronic negotiation 13 electronic negotiation module 28 for the settlement amount. If the settlement amount is declined, the negotiation calculates another settlement amount which is communicated to the medical provider 50.

To accomplish this, a patient initially inputs billing information 26 for a bill owed to a medical provider 50 utilizing the GUI 11 of the patient smartphone 34. Along with the billing information 26, the patient inputs patient information 24 including payment information such as credit card information or checking account information is entered using the electronic negotiation mobile app 32. In another embodiment, the payment information comprises online payment service account information such as a PayPal™ account or the like. After the patient's billing and patient information have been entered, the electronic negotiation module 28 utilizes a negotiation algorithm to calculate the best settlement amount to offer the medical provider. For example, the electronic negotiation module 28 will calculate the settlement amount utilizing a percentage of the owed amount for each bill. In another embodiment, the electronic negotiation module 28 determines the settlement amount utilizing a negotiation table which stores optimal settlement amounts for various balance amounts utilizing one or more lookup tables (LUTs) 30. In another embodiment, the settlement amount can be user-entered values.

After the electronic negotiation module 28 determines a settlement amount for a particular bill, the electronic negotiation module 28 transmits an electronic communication (email, fax, automated voice phone call, etc.) which enables the medical provider to accept or decline the settlement amount. For example, an electronic mail message is sent to the medical provider with a clickable link that includes accept or decline fields. Clicking on the accept or decline link within the email automatically updates the bill's status with the medical provider's response and, if accepted, directs the medical provider to another website to sign the settlement amount with a dated time stamp which is stored in the patient billing information 22. If the medical provider does not have an electronic mail account, the electronic negotiation module 28 transmits an electronic fax message to the medical provider's fax machine. The medical provider indicates on the transmitted document whether the settlement amount is accepted or declined and faxes the document back to the electronic negotiation module 28. The electronic negotiation module 28 utilizes one or more word or image recognition algorithms (e.g., optical character recognition or some other suitable algorithm) to determine whether the settlement amount was accepted or declined which is updated on the bill's status.

After a settlement amount is accepted by the medical provider, the patient is electronically informed by electronic mail and has a predetermined time to pay the medical provider the settlement amount. If the settlement amount is accepted by the medical provider, the patient is charged a service fee for the service provided. The service fee can include a one-time fee, a percentage of the settlement amount, and the like. If the settlement amount is declined by the medical provider, the patient is informed electronically and the electronic negotiation module 28 calculates a second settlement amount via the negotiation algorithm, look-up table, or user-input which is communicated to the medical provider. If the medical provider declines the second settlement amount, the patient is informed once again and is not charged the service fee.

As previously mentioned, the system 10 comprises the processor 14 that executes, and the memory device 16 that stores, computer-executable instructions and/or computer-readable data (e.g., a software package or product) for performing the various techniques and/or methods described herein. The memory device 16 may be a computer-readable recording medium on which a control program or software product is recorded, such as a disk, hard drive, or database 20. Common forms of computer-readable media include, for example, floppy disks, flexible disks, hard disks, magnetic tape, or any other magnetic storage medium, CD-ROM, DVD, or any other optical medium, a ROM, a PROM, an EPROM, a FLASH-EPROM, or other memory chip or cartridge, or any other tangible medium from which a computer can read and use. Alternatively, the methods may be implemented in a transmittable carrier wave in which the control program is embodied as a data signal using transmission media, such as acoustic or light waves, such as those generated during radio wave and infrared data communications, and the like.

Figure 2:
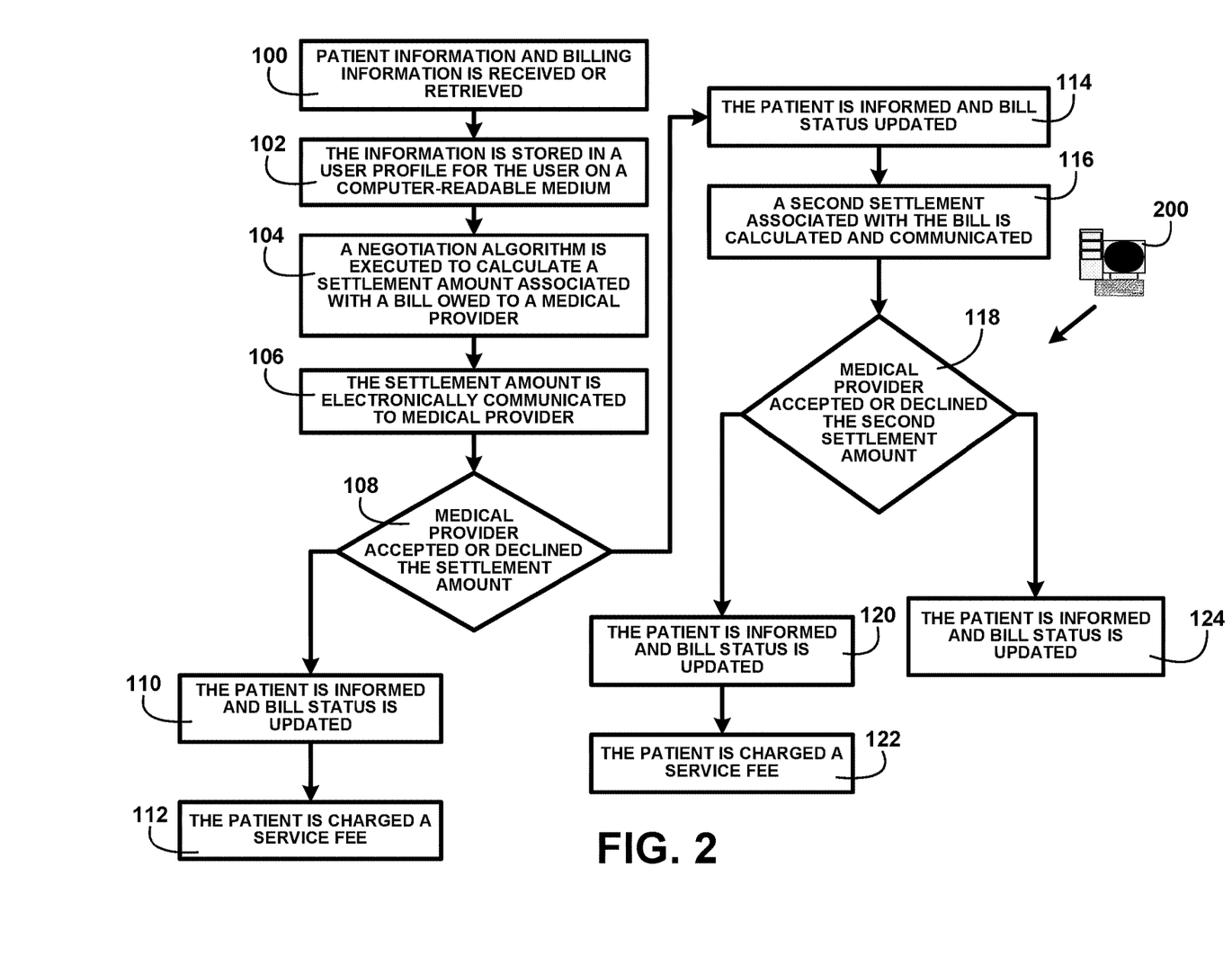
FIG. 2 illustrates a method for automated bill negotiation in accordance with various aspects described herein of one embodiment.

Data Processing for Price and Electronic Negotiation of Patient's Bill Owed:

FIG. 2 illustrates a method related to automatically negotiating a settlement amount for a patient's bill owed to a medical provider, in accordance with various features. While the method is described as a series of acts, it will be understood that not all acts may be required to achieve the described goals and/or outcomes, and that some acts may, in accordance with certain aspects, be performed in an order different than the specific orders described. The method of FIG. 2 may be implemented on a computer 200, as described below. Additionally, it will be appreciated that the method of FIG. 2 may be performed separately or in conjunction with each other.

FIG. 2 illustrates a method for automated bill negotiation, such as can be performed by the system of FIG. 1, in accordance with various aspects described herein. At 100, patient information (e.g., patient name, patient contact information, medical provider, medical provider contact information, insurance carrier, insurance carrier account information, patient payment information, etc.) and billing information (e.g., invoice number, bill amount, patient balance, date of service, negotiated amount to pay, status of the bill, due date, etc.) are received or retrieved. The information is stored in a user profile for the user on a computer-readable medium, at 102. At 104, a negotiation algorithm is executed to calculate a settlement amount (e.g., a dollar amount, or some other currency amount) associated with a bill owed to a medical provider. At 106, the settlement amount is electronically communicated to the medical provider. At 108, it is determined whether the medical provider accepted or declined the settlement amount. If it is determined that the medical provider accepted the settlement amount, the patient is informed, and the bill status is updated at 110. At 112, the patient is charged a service fee. If it is determined that the medical provider declined the settlement amount, the patient is informed, and the bill status is updated at 114. At 116, a second settlement amount associated with the bill is calculated and communicated to the medical provider. At 118, it is determined whether the medical provider accepted or declined the second settlement amount. If it is determined that the medical provider accepted the second settlement amount, the patient is informed, and the bill status is updated at 120. At 122, the patient is charged a service fee. If it is determined that the medical provider declined the second settlement amount, the patient is informed, and the bill status is updated at 124. The method thus provides a bill negotiation tool that is automated and provides the best settlement offer for reducing a patient's bill owed to a medical provider.

The method illustrated in FIG. 2 may be implemented in a computer program product that may be executed on a computer 200 or processor such as the processor 14 in the system of FIG. 1. Further, it is to be appreciated that any suitable computing environment can be employed in accordance with the present embodiments. For example, computing architectures including, but not limited to, stand-alone, multiprocessor, distributed, client/server, minicomputer, mainframe, supercomputer, digital, and analog can be employed in accordance with the present embodiments.

The computer can include a processing unit such as the processor 16 of FIG. 1, a system memory such as the memory device 16 of FIG. 1, and a system bus that couples various system components including the system memory to the processing unit. The processing unit can be any of various commercially available processors (e.g., a central processing unit, a graphical processing unit, etc.). Dual microprocessors and other multi-processor architectures also can be used as the processing unit.

The system bus can be any of several types of bus structure including a memory bus or memory controller, a peripheral bus, and a local bus using any of a variety of commercially available bus architectures. The computer memory device 16 includes read-only memory (ROM) and random-access memory (RAM). A basic input/output system (BIOS), containing the basic routines that help to transfer information between elements within the computer, such as during start-up, is stored in ROM.

The computer can further include a hard disk drive, a magnetic disk drive, e.g., to read from or write to a removable disk, and an optical disk drive, e.g., for reading a CD-ROM disk or to read from or write to other optical media. The computer typically includes at least some form of computer-readable media. Computer-readable media can be any available media that can be accessed by the computer. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules, or other data. Computer storage media includes, but is not limited to, RAM, ROM, EEPROM, flash memory or other memory technology, CD-ROM, digital versatile disks (DVD) or other magnetic storage devices, or any other medium which can be used to store the desired information, and which can be accessed by the computer.

Communication media typically embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above can also be included within the scope of computer-readable media.

A number of program modules may be stored in the drives and RAM, including an operating system, one or more application programs, other program modules, and program non-interrupt data. The operating system in the computer can be any of a number of commercially available operating systems.

A user may enter commands and information into the computer through a keyboard (not shown) and a pointing device or stylus (not shown), such as a mouse. Other input devices (not shown) may include a microphone, an IR remote control, a joystick, a game pad, a satellite dish, a scanner, or the like. These and other input devices are often connected to the processing unit through a serial port interface (not shown) that is coupled to the system bus, but may be connected by other interfaces, such as a parallel port, a game port, a universal serial bus (USB), an IR interface, etc.

A monitor (not shown), or other types of display devices, may also be connected to the system bus via an interface, such as a video adapter (not shown). In addition to the monitor, a computer typically includes other peripheral output devices (not shown), such as speakers, printers, etc. The monitor can be employed with the computer to present data that is electronically received from one or more disparate sources. For example, the monitor can be an LCD, plasma, CRT, etc. type that presents data electronically. Alternatively, or in addition, the monitor can display received data in a hard copy format such as a printer, facsimile, plotter, etc. The monitor can present data in any color and can receive data from the computer via any wireless or hard wire protocol and/or standard.

The computer can operate in a networked environment using logical and/or physical connections to one or more remote computers, such as a remote computer(s). The remote computer(s) can be a workstation, a server computer, a router, a personal computer, a microprocessor-based entertainment appliance, a peer device, or other common network nodes, and typically includes many or all of the elements described relative to the computer. The logical connections depicted include a local area network (LAN) and a wide area network (WAN). Such networking environments are commonplace in offices, enterprise-wide computer networks, intranets, and the Internet.

When used in a LAN networking environment, the computer is connected to the local network through a network interface or adapter. When used in a WAN networking environment, the computer typically includes a modem, or is connected to a communications server on the LAN, or has other means for establishing communications over the WAN, such as the Internet. In a networked environment, program modules depicted relative to the computer, or portions thereof, may be stored in the remote memory device 16. It will be appreciated that network connections described herein are exemplary and other means of establishing a communications link between the computers may be used.

Figure 3:
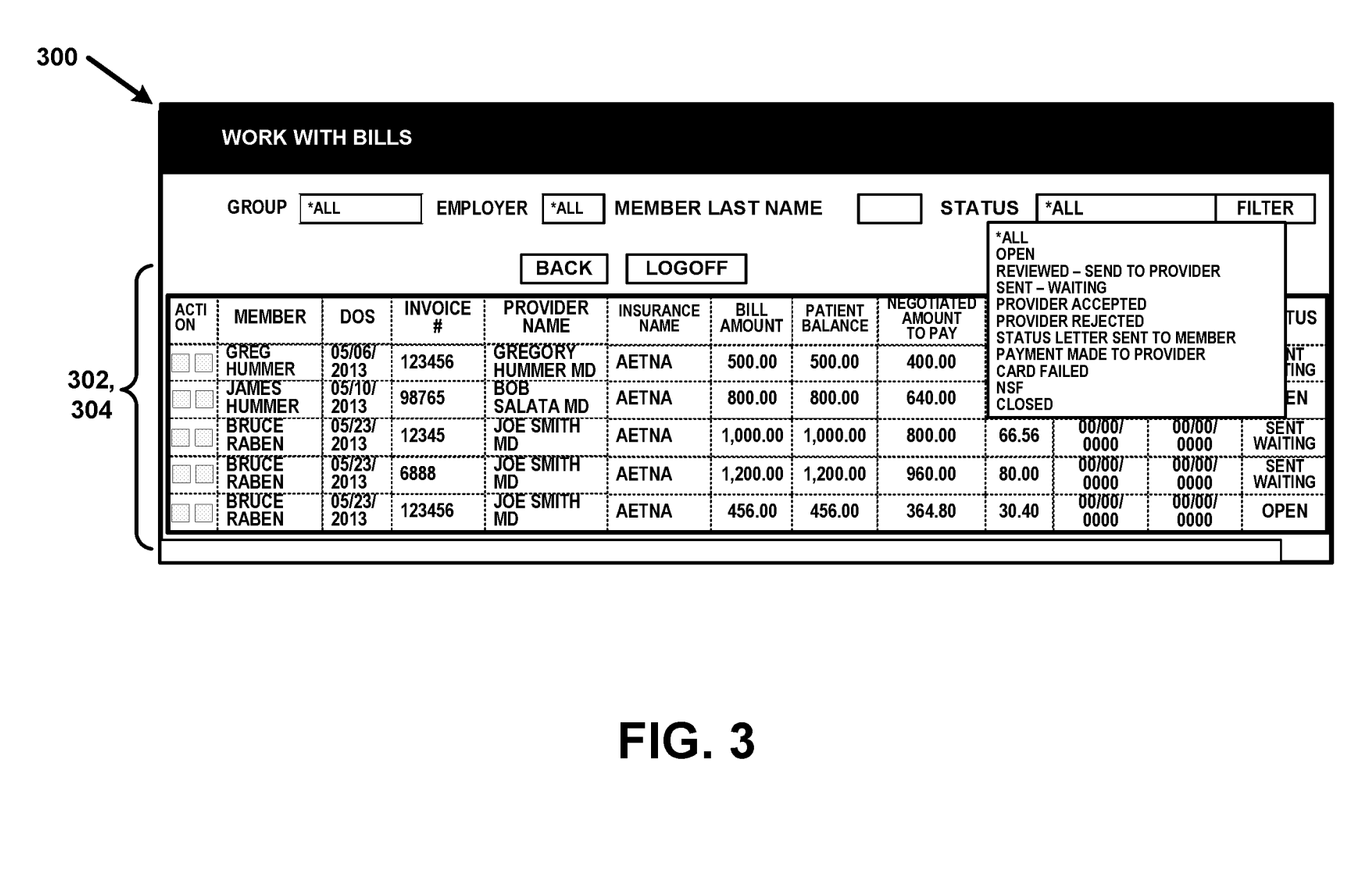
FIG. 3 illustrates a screenshot of a user interface of the automated data processing cost and price determination with electronic negotiation that is presented to a user, in accordance with various aspects set forth herein of one embodiment.

Automated Bill Negotiation:

FIG. 3 illustrates a screenshot of a user interface 300 of the automated bill negotiation that is presented to a user, in accordance with various aspects set forth herein. The user interface 300 includes a personal information field 302 in which information that is entered and/or presented is displayed including but not limited to patient name, medical provider name, and insurance carrier. The user interface 300 also includes a billing information field 304 in which information that is entered and/or present is displayed including but not limited to invoice number, bill amount, patient balance, date of service, negotiated amount to pay, status of the bill, and due date.

Figure 4:
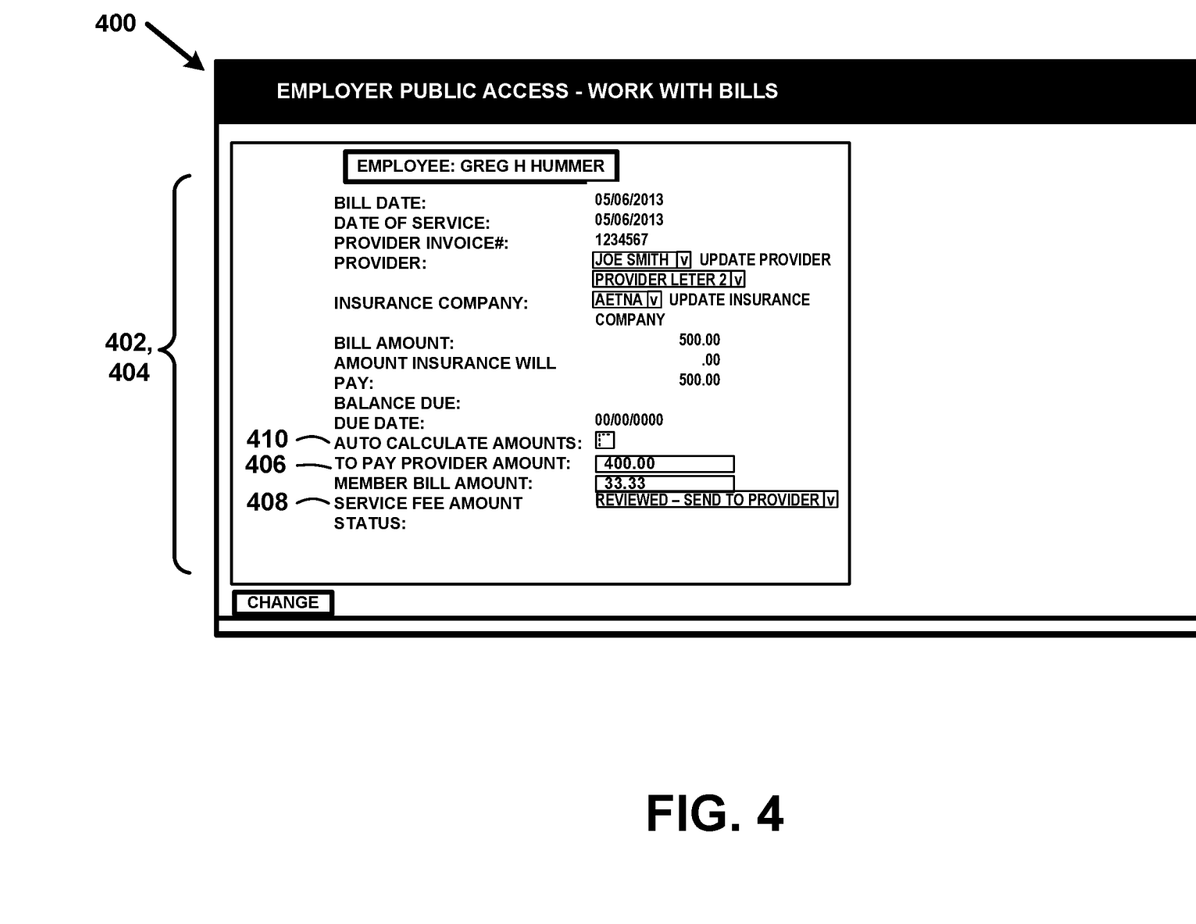
FIG. 4 illustrates another screenshot of a user interface of the automated data processing cost and price determination with electronic negotiation that is presented to a user, in accordance with various aspects set forth herein of one embodiment.

User Interface:

FIG. 4 illustrates another screenshot of a user interface 400 of the automated bill negotiation that is presented to a user, in accordance with various aspects set forth herein. The user interface 400 displays the patient information field 402 and billing information field 404 for a particular bill associated with a patient. The personal information field 402 includes but is not limited to patient name, medical provider name, and insurance carrier, and the billing information field 404 includes but is not limited to invoice number, bill amount, patient balance, date of service, negotiated amount to pay, status of the bill, and due date. The user interface 400 also includes the settlement amount to be paid 406 and a service fee amount status 408. The user interface 400 also includes an auto calculate icon 410 which enables the user to have the automated bill negotiation automatically calculate the settlement amount to be presented to the medical provider.

Figure 5:
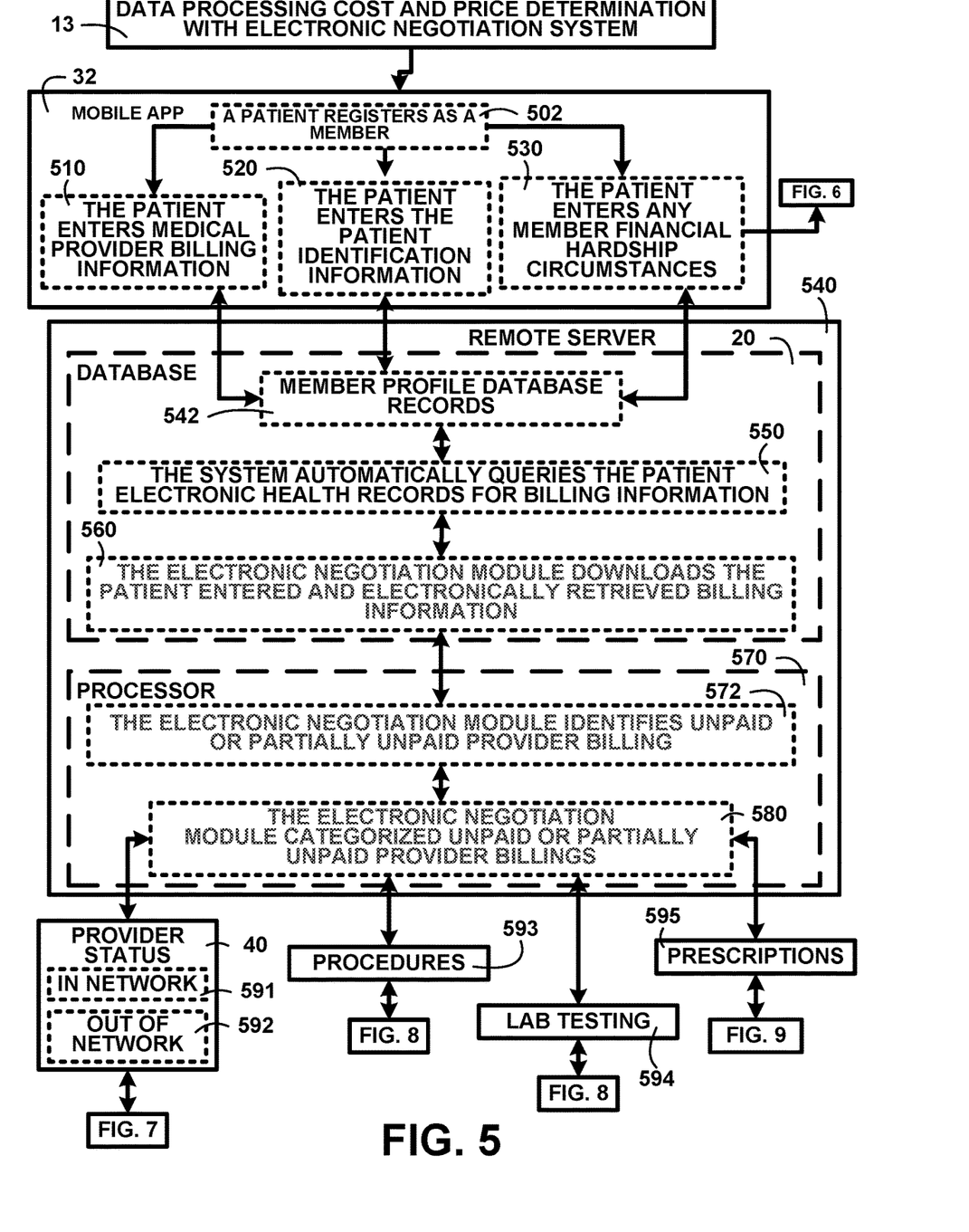
FIG. 5 shows a block diagram of an overview of an electronic negotiation mobile app of one embodiment.

Electronic Negotiation Mobile App:

FIG. 5 shows a block diagram of an overview of an electronic negotiation mobile app of one embodiment. FIG. 5 shows the data processing cost and price determination with electronic negotiation 13 communicating data to the electronic negotiation mobile app 32 on which a patient registers as a member 502. The patient enters medical provider billing information 510. The patient enters the patient identification information 520.

The data processing cost and price determination with electronic negotiation 13 updates over the internet 18 of FIG. 1 medical prices and treatment qualifying conditions 42 of FIG. 1 and records the data on the database 20. The patient enters any member financial hardship circumstances 530. Descriptions continue on FIG. 6. The electronic negotiation mobile app 32 is wirelessly coupled to a remote server 540. The remote server 540 includes at least one database 20. At least one database 20 stores member profile database records 542. The data processing cost and price determination with electronic negotiation 13 automatically queries the patient electronic health records for billing information 550. The electronic negotiation module downloads the patient entered and electronically retrieved billing information 560.

The remote server 540 includes at least one processor 570. At least one processor 570 coupled to the electronic negotiation module 28 of FIG. 1. The electronic negotiation module identifies unpaid or partially unpaid provider billing 572. The electronic negotiation module categorized unpaid or partially unpaid provider billings 580 are further categorized with the provider status 40. The provider status 40 includes in network 591 and out of network 592. The provider status 40 impacts on a patient's billing are described in FIG. 7. The patient's provider billings include procedures 593. The provider status 40 impacts the costs of provider procedures 593 is described in FIG. 8. The patient's provider billings include lab testing 594. The provider status 40 impact on the costs of provider lab testing 594 orders is described on FIG. 8. The provider's prescriptions 595 written for the patient, has a big impact on the medical costs for the patient. Descriptions continue on FIG. 9 of one embodiment.

Figure 6:
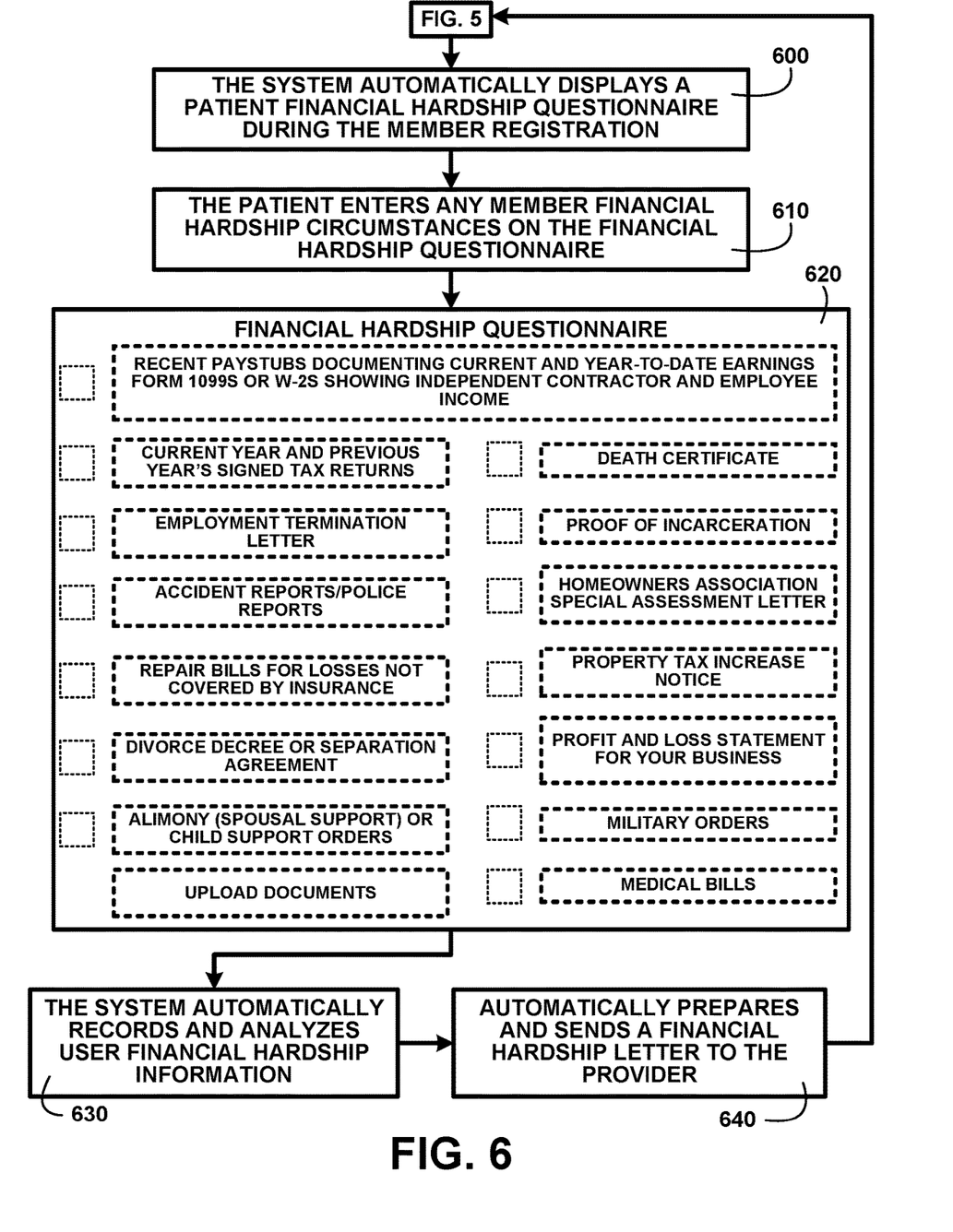
FIG. 6 shows a block diagram of an overview of a patient financial hardship questionnaire of one embodiment.

Patient Financial Hardship Questionnaire:

FIG. 6 shows a block diagram of an overview of a patient financial hardship questionnaire of one embodiment. FIG. 6 shows a continuation from FIG. 5. The system automatically displays a patient financial hardship questionnaire during the member registration 600. The patient enters any member financial hardship circumstances on the financial hardship questionnaire 610. Financial hardship questionnaire 620. The system automatically records and analyzes user financial hardship information 630. Automatically prepares and sends a financial hardship letter to the provider 640 of one embodiment.

Figure 7:
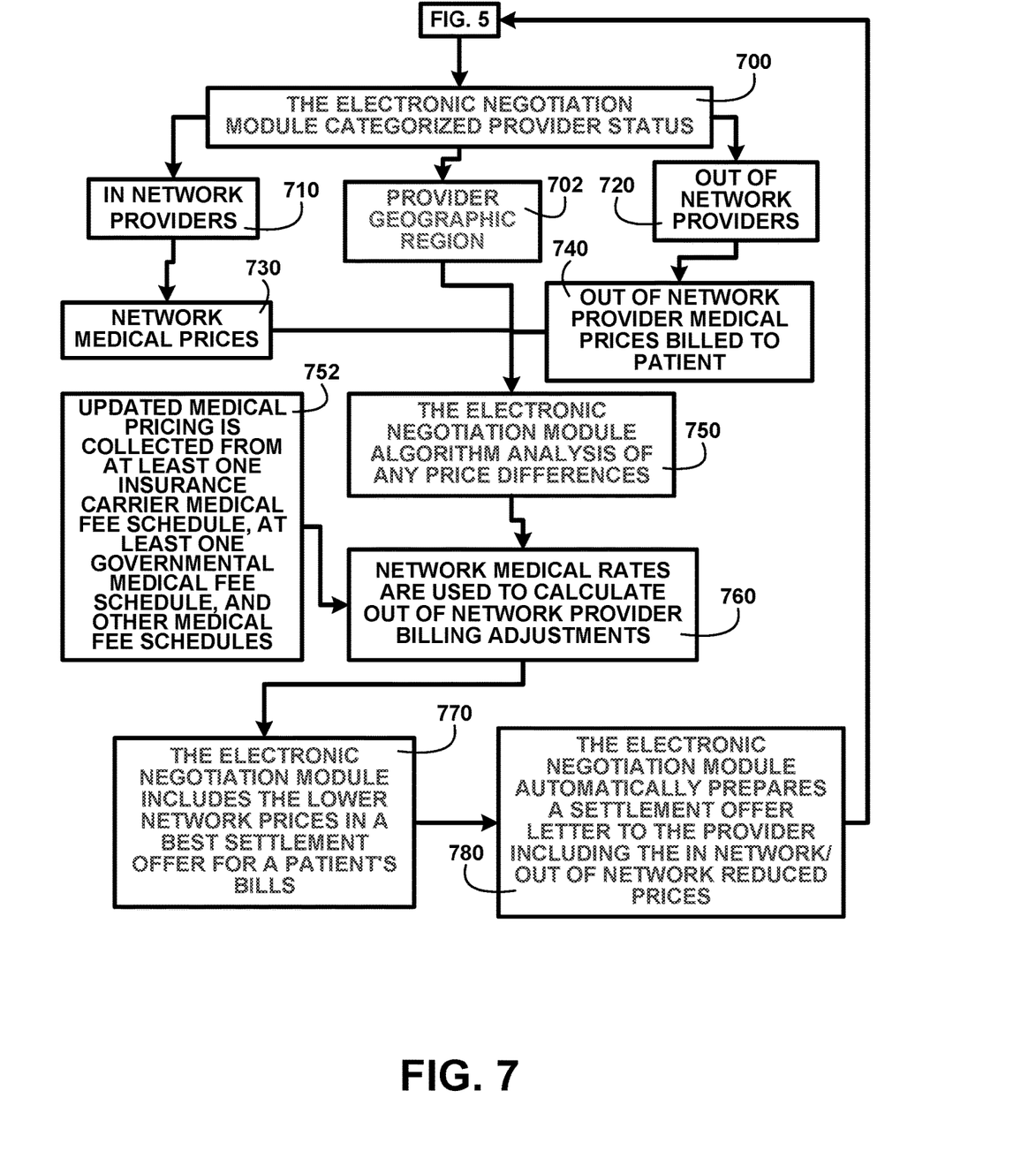
FIG. 7 shows a block diagram of an overview of categorized provider status of one embodiment.

Categorized Provider Status:

FIG. 7 shows a block diagram of an overview of the categorized provider status of one embodiment. FIG. 7 shows a continuation from FIG. 5. The electronic negotiation module categorized provider status 700 includes at least in-network providers 710, out-of-network providers 720, and the provider geographic region 702.

The electronic negotiation module automatically downloads updated in-network providers 710 network medical prices 730 and compares those to out-of-network provider medical prices billed to patient 740. The electronic negotiation module algorithm analysis of any price differences 750. Updated medical pricing is collected from at least one insurance carrier medical fee schedule, at least one governmental medical fee schedule, and other medical fee schedules 752. Network medical rates are used to calculate out-of-network provider billing adjustments 760. The electronic negotiation module includes the lower network prices in a best settlement offer for a patient's bills 770. The electronic negotiation module automatically prepares a settlement offer letter to the provider including the in-network/out-of-network reduced prices 780 of one embodiment.

The electronic negotiation module 28 of FIG. 1 includes a review of the provider billings compliance with local, state, and federal regulations and requirements for providers and facilities. The electronic negotiation module 28 of FIG. 1 determines if the provider gave the patient a required good faith estimate. If the provider conveyed a good faith estimate are the estimate charges substantially in excess of the good faith estimate. The electronic negotiation module 28 of FIG. 1 discounts the provider billing by any excess greater than the good faith estimate.

The federal regulations and requirements for providers and facilities prohibit providers and facilities from directly billing individuals for the difference between the amount they charge and the amount that the individual's plan or coverage will pay plus the individual's cost-sharing amounts in a process referred to as balance billing. The electronic negotiation module 28 of FIG. 1 discounts the provider billing by any balance billing amounts determined with the remote server 540 of FIG. 5 at least one processor 570 of FIG. 5. The federal regulations and requirements for providers and facilities limit billed amounts in situations where a provider's network status changes mid-treatment. The electronic negotiation module 28 of FIG. 1 discounts provider billed amounts to in-network amounts should the provider status change to out-of-network.

Figure 8:
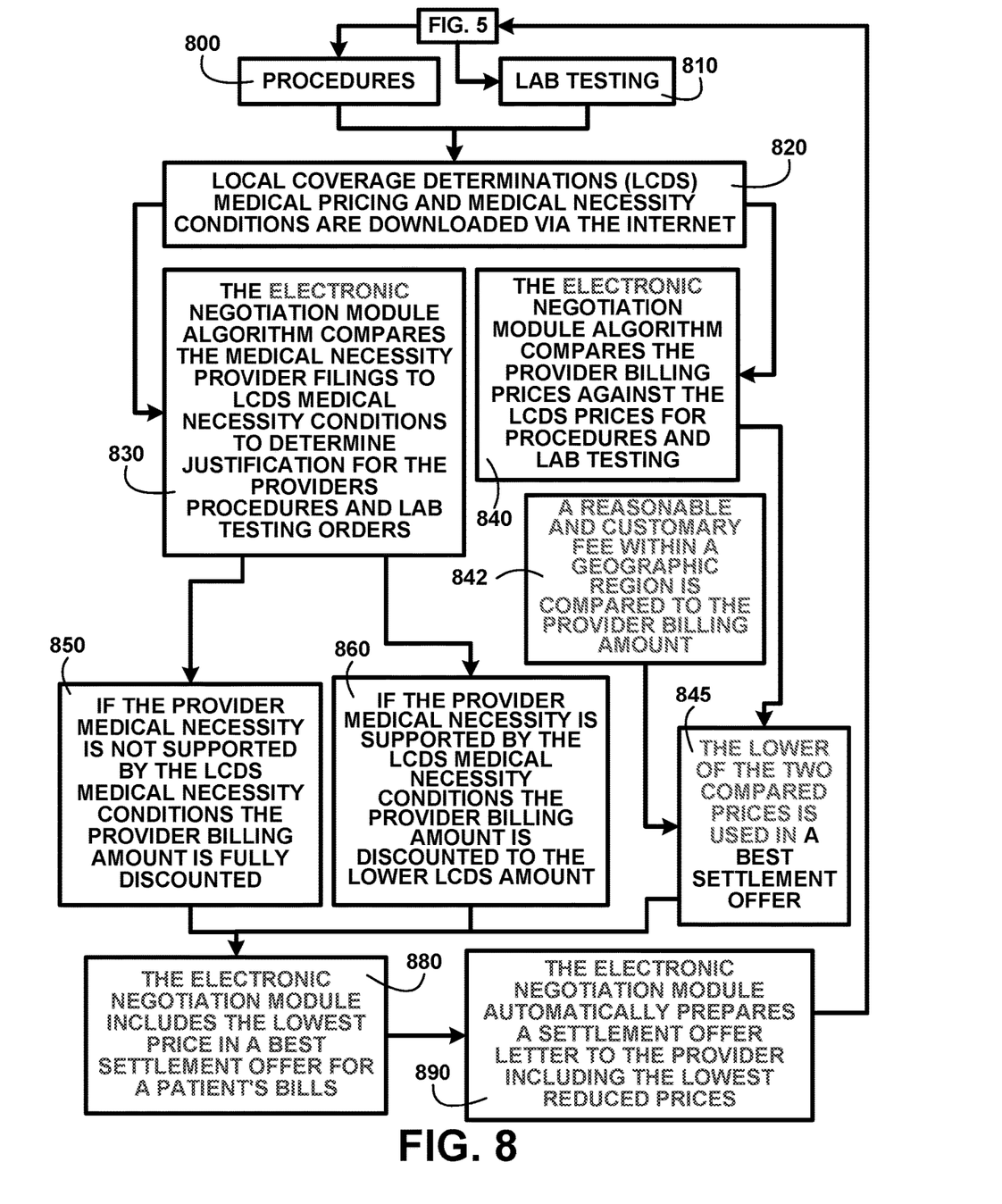
FIG. 8 shows a block diagram of an overview of medical pricing of one embodiment.

Medical Pricing:

FIG. 8 shows a block diagram of an overview of medical pricing of one embodiment. FIG. 8 shows a continuation from FIG. 5. Medical procedures 800 and lab testing 810 are compared with local coverage determinations (LCDS) medical pricing and medical necessity conditions are downloaded via the internet 820. The electronic negotiation module algorithm compares the medical necessity provider filings to LCDS medical necessity conditions to determine justification for the provider's procedures and lab testing orders 830. The electronic negotiation module algorithm compares the provider billing prices against the LCDS prices for procedures and lab testing 840. If the provider's medical necessity is not supported by the LCDS medical necessity conditions the provider billing amount is fully discounted 850. If the provider medical necessity is supported by the LCDS medical necessity conditions the provider billing amount is discounted to the lower LCDS amount 860. LCDS medical rates are used to calculate provider procedures and lab testing orders differences with the LCDS medical rates for provider billing adjustments.

The electronic negotiation module 28 of FIG. 1 automatically updates medical codes pricing constantly from the internet by researching government healthcare programs fee schedules, insurance carriers medical fee schedules, and other valid sources for medical pricing. The Current Procedural Terminology (CPT®) set of medical codes, Healthcare Common Procedure Coding System (HCPCS) Level II codes, International Classification of Diseases Procedure Coding System (ICD-10-PCS) codes, International Classification of Diseases Clinical Modification (ICD-10-CM) codes used by physicians, allied health professionals, non-physician practitioners, hospitals, outpatient facilities, and laboratories to describe the procedures and services they perform.

Health insurance carriers create their medical fee schedules according to a calculation called a "reasonable and customary" fee. The reasonable and customary fee is a calculation according to the prevailing average cost of each service within a geographic region. Many physicians, allied health professionals, non-physician practitioners, hospitals, outpatient facilities, and laboratories set their fees with a calculation that produces a price that is 1.5 to 2 times for each CPT® code based on Medicare's fee schedule.

The electronic negotiation module 28 of FIG. 1 automatically compares the patient-provider billing amount to the Medicare CPT® code fee schedule to determine the provider's fee amount overcharge from the Medicare CPT® code fee schedule. A reasonable and customary fee within a geographic region is compared to the provider billing amount 842. The comparison determines if the provider billing amount is greater or less than the prevailing average cost within the provider geographic region 702 of FIG. 7. The electronic negotiation module compares the lower LCDS prices and reasonable and customary fees prevailing average cost-adjusted price. The lower of the two compared prices is used in a best settlement offer 845. The electronic negotiation module includes the lowest price in a best settlement offer for a patient's bills 880. The electronic negotiation module automatically prepares a settlement offer letter to the provider including the lowest reduced prices 890 of one embodiment.

Figure 9:
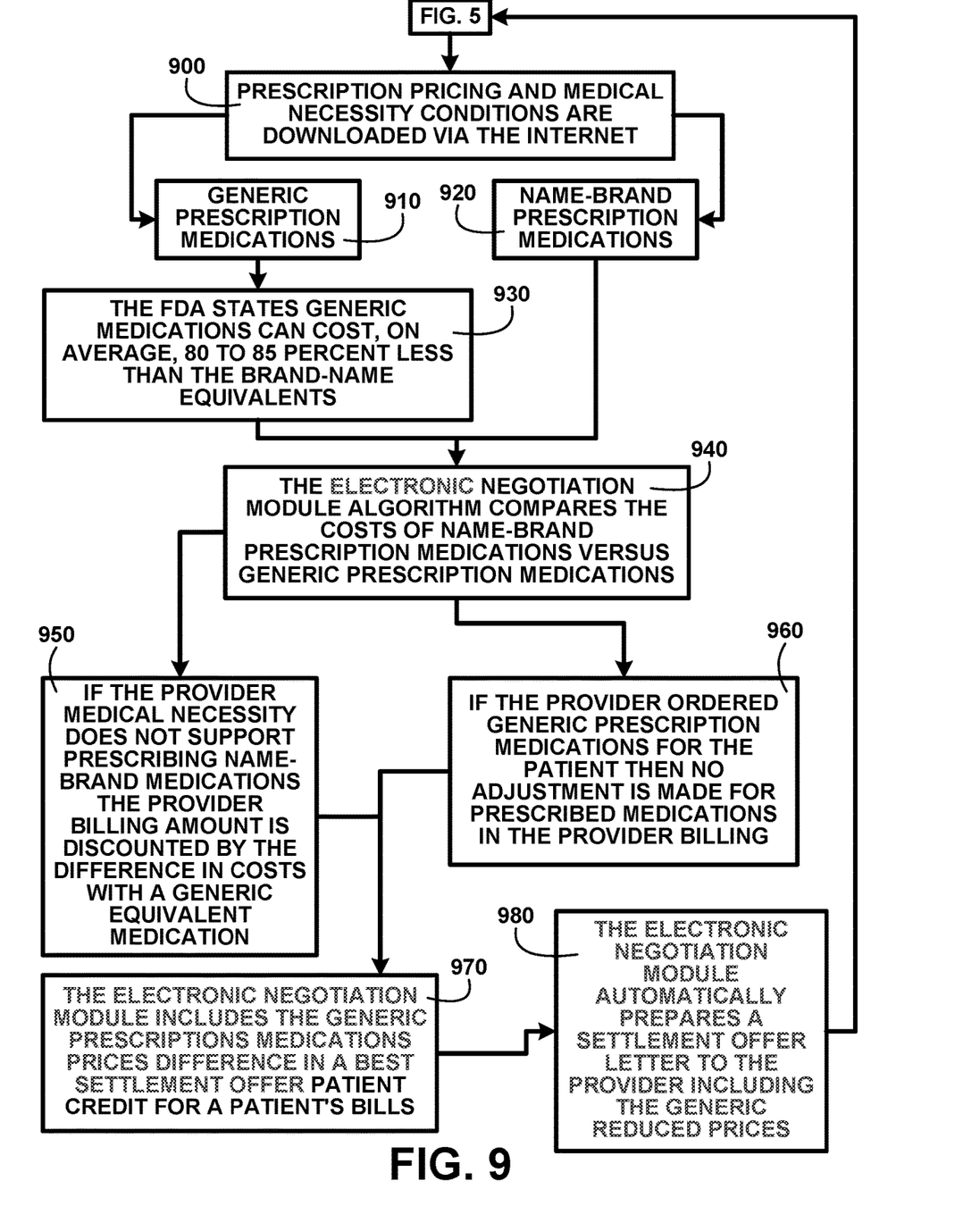
FIG. 9 shows a block diagram of an overview of prescription pricing of one embodiment.

Prescription Pricing:

FIG. 9 shows a block diagram of an overview of prescription pricing of one embodiment. FIG. 9 shows a continuation from FIG. 5. Prescription pricing and medical necessity conditions are downloaded via the internet 900. Generic prescription medications 910 are compared to name-brand prescription medications 920. The FDA states generic medications can cost, on average, 80 to 85 percent less than the brand-name equivalents 930. The electronic negotiation module algorithm compares the costs of name-brand prescription medications versus generic prescription medications 940. If the provider medical necessity does not support prescribing name-brand medications the provider billing amount is discounted by the difference in costs with a generic equivalent medication 950. If the provider ordered generic prescription medications for the patient, then no adjustment is made for prescribed medications in the provider billing 960.

The electronic negotiation module includes the generic prescriptions medications prices difference in a best settlement offer patient credit for a patient's bills 970. The electronic negotiation module automatically prepares a settlement offer letter to the provider including the generic reduced prices 980 of one embodiment. The name-brand medications unsupported prescription is not billed to the patient by the provider. However, the unsupported requirement of the name-brand medications has cost the patient an extra expense. The difference is applied as a credit to the balance of the patient's provider billing amounts as the name-brand medications could not be justified of one embodiment.

The foregoing has described the principles, embodiments, and modes of operation of the present invention. However, the invention should not be construed as being limited to the particular embodiments discussed. The above-described embodiments should be regarded as illustrative rather than restrictive, and it should be appreciated that variations may be made in those embodiments by workers skilled in the art without departing from the scope of the present invention as defined by the following claims.

What is claimed is:

1. A data processing cost and price determination platform with electronic negotiation, comprising:
a first mobile device having a mobile app configured to register a medical patient with unique patient data;
a medical database wirelessly coupled to the mobile app and configured to retrieve and store patient medical necessity codes, the unique patient data and billed medical services related to the registered medical patient of a medical provider;
a server coupled to the medical database configured to electronically collect updated medical pricing data related to the patient billed medical services from governmental and health insurance carriers based on geographical information of the medical provider and medical fee schedule sources and medical necessity standards based on demographics of the medical provider;
a processor coupled to the server configured to execute computer-executable instructions stored on the server to compare the patient billed account data with the updated medical pricing data and to compare the medical necessity standards to the patient medical necessity codes to determine a suggested fair market value of the billed medical services to determine a fair medical cost;
an electronic negotiation module coupled to the processor configured to convert the generated fair market value into a settlement amount for soliciting a negotiated settlement rate from the medical provider that is less than the billed medical services; and
a communication interface operating on a second mobile device and coupled to the server, database and the electronic negotiation module and configured to allow the medical provider via a graphical user interface to either select an acceptance button on the graphical user interface to electronically accept the settlement amount or to select a counter offer button on the graphical user interface to send a counter settlement amount to the first mobile device of the medical patient, wherein the communication interface is further configured to generate an electronic agreement between the medical patient and the medical provider based on either the settlement amount or the counter settlement amount.

2. The data processing cost and price determination platform with electronic negotiation of claim 1, wherein updated medical pricing data includes at least one commercial insurance carrier medical fee schedule and at least one governmental medical fee schedule.

3. The data processing cost and price determination platform with electronic negotiation of claim 1, wherein the updated medical pricing data includes health insurance carriers reasonable and customary fee data based on a prevailing average cost of each service within a medical provider geographic region.

4. The data processing cost and price determination platform with electronic negotiation of claim 1, wherein the updated medical pricing data includes government based local coverage determinations (LCDs) medical pricing, and medical necessity conditions.

5. The data processing cost and price determination platform with electronic negotiation of claim 1, wherein the unique patient data includes patient financial hardship questionnaire responses.

6. The data processing cost and price determination platform with electronic negotiation of claim 1, wherein the unique patient data includes a patient's financial hardship letter to be included in negotiated settlement rate.

7. The data processing cost and price determination platform with electronic negotiation of claim 1, wherein the patient medical necessity codes include International Classification of Diseases (ICD) diagnosis codes.

8. A data processing platform, comprising:
a first mobile device having a mobile app configured to register a medical patient with unique patient data;
a medical database wirelessly coupled to the mobile app and configured to retrieve and store patient medical necessity codes, the unique patient data and billed medical services related to the registered medical patient of a medical provider;
a server coupled to the medical database configured to electronically collect updated medical pricing data related to the patient billed medical services from governmental and health insurance carriers based on geographical information of the medical provider and medical fee schedule sources and medical necessity standards based on demographics of the medical provider;
a processor coupled to the server configured to execute computer-executable instructions stored on the server to compare the patient billed account data with the updated medical pricing data and to compare the medical necessity standards to the patient medical necessity codes to determine a suggested fair market value of the billed medical services to determine a fair medical cost;
an electronic negotiation module coupled to the processor configured to convert the generated fair market value into a settlement amount for soliciting a negotiated settlement rate from the medical provider that is less than the billed medical services; and
a communication module operating on a second mobile device and coupled to the server, database and the electronic negotiation module and configured to allow the medical provider via a graphical user interface to either select an acceptance button on the graphical user interface to electronically accept the settlement amount or to select a counter offer button on the graphical user interface to send a counter settlement amount to the first mobile device of the medical patient, wherein the communication interface is further configured to generate an electronic agreement between the medical patient and the medical provider based on either the settlement amount or the counter settlement amount.

9. The data processing platform of claim 8, wherein updated medical pricing data includes medical necessity justification according to accepted updated medical data for medical provider services and prescriptions.

10. The data processing platform of claim 8, wherein updated medical pricing data includes a governmental medical fee schedule and a commercial medical fee schedule.

11. The data processing platform of claim 8, wherein the updated medical pricing data includes health insurance carrier reasonable and customary fee data based on a prevailing average cost of each service within a medical provider geographic region.

12. The data processing platform of claim 8, wherein the updated medical pricing data includes local coverage determinations (LCDs) medical pricing and medical necessity conditions.

13. The data processing platform of claim 8, wherein the unique patient data includes patient financial hardship questionnaire responses.

14. The data processing platform of claim 8, wherein the patient custom data includes a patient's financial hardship letter to be included in negotiated settlement rate.

15. A data processing cost and price determination platform, comprising:
   a first mobile device having a mobile app configured to register a medical patient with unique patient data;
   a medical database wirelessly coupled to the mobile app and configured to retrieve and store patient medical necessity codes, the unique patient data and billed medical services related to the registered medical patient of a medical provider;
   a server coupled to the medical database configured to electronically collect updated medical pricing data related to the patient billed medical services from governmental and health insurance carriers based on geographical information of the medical provider and medical fee schedule sources and medical necessity standards based on demographics of the medical provider;
   a processor coupled to the server configured to execute computer-executable instructions stored on the server to compare the patient billed account data with the updated medical pricing data and to compare the medical necessity standards to the patient medical necessity codes to determine a suggested fair market value of the billed medical services to determine a fair medical cost;
   wherein the processor is further configured to generate a fair market value of the billed medical services based on the fair medical cost and the medical necessity result;
   an electronic negotiation module coupled to the processor configured to convert the generated fair market value into a settlement amount for soliciting a negotiated settlement rate from the medical provider that is less than the billed medical services; and
   a communication module interface operating on a second mobile device and coupled to the server, database and the electronic negotiation module and configured to allow the medical provider via a graphical user interface to either select an acceptance button on the graphical user interface to electronically accept the settlement amount or to select a counter offer button on the graphical user interface to send a counter settlement amount to the first mobile device of the medical patient, wherein the communication module is further configured to generate an electronic agreement between the medical patient and the medical provider based on either the settlement amount or the counter settlement amount.

16. The data processing cost and price determination platform of claim 15, wherein the patient medical necessity codes include International Classification of Diseases (ICD) diagnosis codes.

17. The data processing cost and price determination platform of claim 15, wherein the updated medical pricing data includes local coverage determinations (LCDs) medical pricing and medical necessity conditions.

18. The data processing cost and price determination platform of claim 15, wherein the updated medical pricing data includes health insurance carrier reasonable and customary fee data based on a prevailing average cost of each service within a medical provider geographic region.

19. The data processing cost and price determination platform of claim 15, wherein the medical billing codes comprises Current Procedural Terminology (CPT) codes.

20. The data processing cost and price determination platform of claim 15, wherein the unique patient financial hardship data comprises patient financial hardship questionnaire responses.

* * * * *